(12) United States Patent
Shaw et al.

(10) Patent No.: US 8,394,648 B2
(45) Date of Patent: Mar. 12, 2013

(54) METHOD OF FABRICATION OF PHOTONIC BIOSENSOR ARRAYS

(75) Inventors: Andrew Mark Shaw, Exeter (GB); Rouslan Vladimir Olkhov, Devonshire (GB)

(73) Assignee: Attomarker Limited (GB)

( * ) Notice: Subject to any disclaimer, the term of this patent is extended or adjusted under 35 U.S.C. 154(b) by 203 days.

(21) Appl. No.: 12/679,219

(22) PCT Filed: Mar. 19, 2008

(86) PCT No.: PCT/GB2008/050200
§ 371 (c)(1), (2), (4) Date: Jul. 6, 2010

(87) PCT Pub. No.: WO2008/117086
PCT Pub. Date: Oct. 2, 2008

(65) Prior Publication Data
US 2011/0294679 A1 Dec. 1, 2011

(30) Foreign Application Priority Data

Mar. 23, 2007 (GB) .................................. 0705604.7

(51) Int. Cl.
*G01N 33/53* (2006.01)

(52) U.S. Cl. ........ 436/809; 436/149; 436/164; 436/172; 436/174; 436/518; 436/805; 422/68.1; 422/82.05; 422/82.06; 422/82.08; 422/82.09; 422/82.11; 422/407; 435/164; 435/165; 435/283.1; 435/287.1; 435/287.2; 435/4; 435/5; 435/7.2; 435/7.9; 356/369; 506/9

(58) Field of Classification Search .................. 422/68.1, 422/82.05, 82.06, 82.08, 82.09, 82.11, 99, 422/407; 435/164, 165, 283.1, 287.1, 287.2, 435/4, 5, 7.2, 7.9; 436/149, 164, 172, 174, 436/518, 805, 809; 356/369; 506/9
See application file for complete search history.

(56) References Cited

FOREIGN PATENT DOCUMENTS
WO WO 92/21973 12/1992

OTHER PUBLICATIONS

Endo et al, "Multiple Label-Free Detection of Antigen-Antibody Reaction Using Localized Surface Plasmon Resonance-Based Core-Shell Structured Nanoparticle Layer Nanochip", Anal. Chem. 2006, 78, pp. 6465-6475.*

(Continued)

*Primary Examiner* — Dennis M White
(74) *Attorney, Agent, or Firm* — Snell & Wilmer L.L.P.

(57) ABSTRACT

This invention relates to a method for the fabrication of photonic biosensor arrays and applications of arrays produced by the method in the biomedical field. A method for the fabrication of a biosensor array for plasmon resonance-based sensing of a plurality of different biological targets simultaneously, the method comprising: (i) providing a transparent substrate; ii) providing seed metallic nanoparticles in the form of a colloid; (iii) depositing said colloid as discrete metallic islands on the transparent substrate, each of said metallic islands comprising a plurality of metallic nanoparticles; (iv) washing the substrate in order to remove unadhered material; (v) developing the substrate in a growth solution, which solution comprises a salt of the same metal which is present in the form of discrete metallic islands on the substrate, a reducing agent, a capping agent and optionally a surfactant; (vi) washing the developed substrate; and (vii) functionalising each of said metallic islands with a different functionalising molecule using a common chemical process to attach said different functionalising molecules to said metallic islands.

20 Claims, 6 Drawing Sheets

OTHER PUBLICATIONS

Shumaker-Parry et al, "Parallel, Quantitative Measurement of Protein Binding to a 120-Element Double-Stranded DNA Array in Real Time Using Surface Plasmon Resonance Microscopy" Anal. Chem. 2004, pp. 2071-2082.*

Olkhov, R.V. and Shaw, A.M., "Label-free antibody-antigen binding detection by optical sensor array based on surface-synthesized gold nanoparticles," Biosensor & Bioelectronics, Elsevier Science Publishers, Barking, GB, vol. 23, No. 8, Dec. 15, 2007, pp. 1298-1302.

Xiang, Y., et al., "Seed-mediated growth of gold nanoparticles using self-absembled monolayer of polystyrene microspheres as nanotemplate arrays," Chinese Physics Chinese Phys. Soc. China, vol. 15, No. 9, Sep. 2006, pp. 2080-2086.

Iqbal, M., and Tae, G., "Unstable Reshaping of Gold Nanorods Prepared by a Wet Chemical Method in the Presence of Silver Nitrate," Journal of Nanoscience and Nanotechnology, American Scientific Publishers, US, vol. 6, No. 11, Nov. 1, 2006, pp. 3355-3359.

Sumerel, J., et al., "A Digital Printing of Bioinks," IS&T Reporter "The Window of Imaging," (online) vol. 21, No. 5, Sep. 17, 2006-Sep. 22, 2006, pp. 1-8.

ISR and Written Opinion for International Application No. PCT/GB08/50200 dated Jun. 2, 2008.

* cited by examiner

METHOD OF FABRICATION OF PHOTONIC BIOSENSOR ARRAYS

CROSS-REFERENCE TO RELATED APPLICATIONS

This application is U.S. national phase filing under 35 U.S.C. §371 of PCT/GB2008/050200 filed Mar. 19, 2008 and claims priority from United Kingdom Application No. GB 07055604.7 which was filed on Mar. 23, 2007.

FIELD OF THE INVENTION

This invention relates to a method for the preparation of photonic biosensor arrays and applications of arrays produced by the method in the biomedical field.

This application relates to UK patent application number 0705594.0 (and to the corresponding PCT application number PCT/GB2008/050202, filed on the same day as this application by the same applicant), the entire contents of both of which are hereby incorporated by reference.

BACKGROUND TO THE INVENTION

Plasmon absorption in metal nanoparticles is highly dependent on nanoparticle shape, size, and dielectric constant of the surrounding medium. Strong plasmon absorption and sensitivity to local environment have made metal nanoparticles attractive candidates as sensors for a range of analytes including DNA, metal ions, and antibodies.

Much of the work in this area has focussed on the use of suspensions of metals, especially "noble" metals such as gold or silver, gold being particularly suitable in view of its biocompatibility.

For example, in WO 2006/137851 (Virginia Tech Intellectual Properties Inc.) the preparation of a metallic suspension by the direct coating of silica nanoparticles by gold or silver is reported. A method is described of making a metallic suspension, involving the activation of silica particles in a silica colloidal suspension; the nucleation of noble metal atoms to the silica particles in the suspension and the subsequent growth of noble metal particles on the silica particles at the nucleation sites.

WO 2006/099312 (North-Western University) relates to a Method of Producing Gold Nanoprisms and is also concerned with metallic suspensions.

WO 2006/065762 (University of South Carolina) and WO 2006/066180 (Intel Corporation) relate to Surface Enhanced Raman Spectroscopy (SERS) facilitated by the use of gold nanoparticles, though the materials provided employ continuous metallic surfaces.

A more powerful method of utilising the interesting photonic properties of nanoparticles would be to provide the nanoparticles in the form of a 2D photonic array.

In general a photonic biosensor array, sometimes called a microarray or biochip, comprises a collection of probe spots to which different targets may attach. For example in the case of a DNA microarray the probes are oligonucleotides, cDNA or similar which are hybridised with fluorescence labelled samples, typically of two colours, one for the patient the other for the control. Typically, fluorescence from the hybridised array is then viewed to determine to which spots binding has occurred. There are other types of array such as protein arrays (including antibody arrays) where spots of protein molecules (or antibodies) are used to identify the complementary entity (antibodies or proteins). Thus chemical compound arrays may be employed to search for proteins and other biologically active molecules again by employing functionalising molecules or entities in an array of spots which bind with specific biological targets. In general, however, all these techniques employ fluorescence labelling of the targets to detect binding events on the array.

The arrays provided by the methods of the present invention do not employ fluorescence but instead rely upon plasmon resonance-based sensing. Broadly speaking in this technique total internal reflection of light is used to generate an evanescent wave which excites plasmons (a collective electronic excitation) in a metallic conductor, which are modified by the presence of a target molecule on the surface of the conductor. The modification results in a shift, generally in both wavelength and amplitude, of the plasmon resonance peak detectable in the totally internally reflected light. Plasmon resonance-based sensing has the ability to detect very small changes in the effective refractive index in a medium adjacent the surface of the metallic conductor, for example down to $\Delta n$ of the order of $10^{-4}$ refractive index units (RIU).

It is known to employ label-free surface plasmon resonance (SPR) based technology for studying biomolecular interaction in real time and, in particular, technology for this is available from the Swedish company BIAcore AB; for background technical information see published BIAcore patent applications such as WO 2006/135309, WO 94/00751, U.S. Pat. No. 4,997,278, and WO 97/19375. However BIAcore provide materials employing a continuous metal surface. Some further technical background information relating to plasmon resonance-based sensing in a different context (evanescent wave cavity ringdown spectroscopy) can be found in EvanesCo patent application WO 2005/088277.

There is, however, a need to provide an improved method of preparation of photonic arrays suitable for use in a wide variety of assay techniques, and in particular leading to assay techniques with increased sensitivity.

Embodiments of the techniques we describe provide a step towards solutions of these problems.

SUMMARY OF THE INVENTION

According to a first aspect of the invention there is therefore provided a method for the fabrication of a biosensor array for plasmon resonance-based sensing of a plurality of different biological targets simultaneously, the method comprising:
(i) providing a transparent substrate;
(ii) providing seed metallic nanoparticles in the form of a colloid;
(iii) depositing said colloid as discrete metallic islands on the transparent substrate, each of said metallic islands comprising a plurality of metallic nanoparticles;
(iv) washing the substrate in order to remove unadhered material;
(v) developing the substrate in a growth solution, which solution comprises a salt of the same metal which is present in the form of discrete metallic islands on the substrate, a reducing agent, a capping agent and optionally a surfactant;
(vi) washing the developed substrate; and
(vii) functionalising each of said metallic islands with a different functionalising molecule using a common chemical process to attach said different functionalising molecules to said metallic islands.

Thus the invention provides a seed-mediated method for nanoparticle growth directly on a substrate surface. This allows tag-free specific binding of biomolecules observed on a sensor array based on grown-on-surface particles. Having the ability to use an uncoated substrate obviates the need for one or more pattern control layers.

In a related aspect the invention also provides a biosensor array for plasmon resonance-based sensing of a plurality of different biological targets, the array obtained by or obtainable from the method of this first aspect of the invention.

The metallic nanoparticles are typically selected from the group comprising copper, silver, gold, platinum, palladium and iridium or a mixture or an alloy thereof. Gold nanoparticles are preferred. In the latter case, advantageously in the development step (v), the gold salt comprises $HAuCl_4$ or a potassium, calcium, sodium, or lithium salt thereof.

In accordance with a preferred embodiment, in step (ii) of the method of the invention, the seed metallic nanoparticles are substantially spherical with a diameter typically in the range of from 2 to 6 nm, more preferably in the range of from 3 to 4 nm. In accordance with a particularly preferred embodiment, 3-4 nm spherical seeds may be produced by reduction of $Au^{3+}$ (for example $3 \times 10^{-4}$ M $HAuCl_4$) by excess of $NaBH_4$ ($3 \times 10^{-3}$ M) in the presence of tri-sodium citrate capping agent ($3 \times 10^{-4}$ M).

The seed particle colloid is typically printed in an array of spots on uncoated silica or glass surface and the slides are allowed to dry. The printed seed density (in terms of number of particles per unit of surface area) determines the density of the grown particles, therefore one can easily achieve practically any desired surface coverage.

In accordance with a preferred embodiment of the method of the invention, in development step (v), the growth solution comprises a metal salt, a reducing agent and a capping agent. The capping agent may function additionally as a surfactant and a capping agent is preferred which, following deposition of the small seed nanoparticles, facilitates growth of the larger "crystals" in a sterically hindered environment. A capping agent based on cetyltrimethylammonium halide, and particularly the bromide (CTAB), is particularly preferred.

In accordance with a preferred method the surfactant is selected from the group comprising or consisting of tetrabutylammonium bromide, dodecyldimethylammonium bromide, cetyltrimethylammonium bromide; the capping agent is cetyltrimethylammonium bromide (CTAB) and the reducing agent is ascorbic acid.

Other suitable reducing agents are typically selected from the group comprising sodium citrate, formaldehyde, 2-mercaptoethanol, dithiothreitol, and hydrazine.

Advantageously, the reducing agent is used in a concentration of from $1 \times 10^{-6}$ M to use as the solvent itself, more preferably of from $1 \times 10^{-5}$ M to $1 \times 10^{-2}$ M and more preferably still of from $2 \times 10^{-4}$ M to $9 \times 10^{-4}$ M; the substrate is exposed to growth solution for a time in the region of from 5 minutes to 100 minutes, more preferably of from 15 minutes to 40 minutes and more preferably still of from 20 to 30 minutes; and the temperature at which the substrate is exposed to growth solution is of from 0 to 95 degrees Celsius; more preferably in the region of from 20 to 80 degrees Celsius, and more preferably still of from 25 to 30 degrees Celsius.

The functionalising step (vii) advantageously comprises using a solution deposition head with a plurality of nozzles to collect a plurality of said different functionalising molecules from a plurality of reservoirs and to deposit said plurality of functionalising molecules onto a respective plurality of said metallic islands.

Different functionalising molecules may be attached to said metallic nanoparticles using the same ligand. The functionalising molecules are particularly varied, for example proteins, antibodies, DNA/RNA strains, aptomers, chelating agents and sequestering agents.

In certain preferred embodiments of the method of the invention, in functionalising step (vii), a fraction of the respective plurality of said metallic islands are left un-functionalised and instead comprise a plurality of control spots.

It has been observed that when a further source of metal ions is provided in development step (v) of this first method of the invention, wherein this further source of metal ions is different to the metal forming the plurality of metallic islands, a closer degree of control is possible as regards the resultant size distribution of the grown nanoparticles.

Accordingly, in a second main aspect, the present invention provides a method for controlling the size distribution of nanoparticles grown in accordance with the following steps:
(i) provision of a transparent substrate;
(ii) provision of seed metallic nanoparticles in the form of a colloid;
(iii) deposition of said colloid as discrete metallic islands on the transparent substrate, each of said metallic islands comprising a plurality of metallic nanoparticles;
(iv) washing of the substrate in order to remove unadhered material;
(v) development of the substrate in a growth solution, which solution comprises a salt of the same metal which is present in the form of discrete metallic islands on the substrate, a reducing agent, a capping agent and optionally a surfactant;
which method comprises adding metal ions to the growth solution of development step (v), wherein these additional metal ions are different to the metal forming the plurality of metallic islands on the substrate.

In accordance with a related aspect, the substrates bearing the nanoparticles with controlled size distribution resulting form the method of this second aspect of the invention then undergo the following further steps: (vi) washing; and
(vii) functionalisation of each of said metallic islands with a different functionalising molecule using a common chemical process to attach said different functionalising molecules to said metallic islands.

In accordance with a particularly preferred embodiment of this second aspect of the invention, the shape as well as the size distribution is observed to be controllable by the addition of the further source of metal ions.

The added metal ions are typically selected from the group comprising copper, silver, gold, platinum, palladium and iridium or a mixture thereof. Silver ions are preferred. The concentration of the additive metal ions is typically in the range of from 0.01% to 1% of the concentration of the metal salt of the growth solution (ie the metal which is present in the form of discrete metallic islands on the substrate); more preferably from 0.05% to 0.95% of the concentration of the metal salt of the growth solution; more preferably from 0.1% to 0.9% of the concentration of the metal salt of the growth solution and more preferably still from 0.25% to 0.75% of the concentration of the metal salt of the growth solution. Advantageously, in order to maximise control of the size distribution of nanoparticles grown, the capping agent used will be a cetyltrimethylammonium halide, and particularly preferred is the bromide (CTAB) and the additive metal ions will comprise $Ag^+$.

For example, it was observed that once seeded slides are developed in growth solution containing $2 \times 10^{-4}$ M $HAuCl_4$, 0.1M cetyltrimethylammonium bromide (CTAB) as capping agent, and $4 \times 10^{-4}$ M ascorbic acid as reducing agent for 20-30 minutes at 25° C. a variety of gold nano-shapes was obtained. On addition of $1 \times 10^{-5}$ M $Ag^+$ the size distribution of grown particles was more uniform and gold nanocrystals were highly faceted, which can improve sensitivity to the change of the medium refractive index.

In some preferred embodiments of the first and second aspects of the present invention, the metallic nanoparticles, which are preferably of gold, are highly anisotropic. Furthermore they may have at least one dimension of less than 30 nm, preferably less than about 25 nm. At this point the interaction between the evanescent wave and the metal changes from being dominated by absorption to being dominated by scattering. In some preferred embodiments the nanoparticles form optical antennas, that is, in embodiments, pairs of rod-like nanoparticles separated by a gap of similar dimensions to the width of a rod. More generally such an optical antenna may comprise an adjacent pair of nanoparticles, preferably each with a length:width aspect ratio of greater than 2:1, and preferably having adjacent ends separated by a gap of less than 100 nm, preferably less than 50 nm. In some preferred embodiments these comprise rod-shaped nanoparticles but other shaped nanoparticles may also be employed, for example generally triangular nanoparticles, or a combination of different shaped nanoparticles such as a rod-shaped and an adjacent generally triangular nanoparticle.

In particular, preferably each nanoparticle of an adjacent pair of nanoparticles has a length which is resonant for a plasmon wavelength in the metal, more particularly having a length which is approximately equal to an odd integral number of a plasmon half-wavelengths.

The inventors believe that the enhanced electric field in the gap between the nanoparticles also enhances Raleigh scattering, and hence the overall sensitivity of the technique. More generally, employing discrete islands of nanoparticles rather than a continuous surface in a biophotonic array as described above facilitates use of the array for detection of a plurality of different biological targets simultaneously.

Unlike conventional microarrays, embodiments of the above-described array allow the same chemistry to be employed to attach a plurality of different types of functionalising molecule to the metallic nanoparticles of the different islands. Thus whereas conventionally each different fluorescent label requires a separate chemical process to attach the label to a target or potential target, an array of the type we describe is suitable for use with an automated fabrication method.

Thus in a preferred aspect the invention provides a method of fabricating a biosensor array for plasmon resonance-based sensing of a plurality of different biological targets, the array comprising a transparent substrate having a surface bearing a plurality of array spots for plasmon resonance sensing, each of said array spots comprising a discrete metallic island to which is attached functionalising molecules for binding to a said biological target, different said islands bearing different said functionalising molecules for binding to different ones of said biological targets, and wherein total internal reflection of light at said surface at a wavelength at or near a said plasmon resonance results in scattering of said light away from said surface, said scattering being modulated by said binding of said biological targets.

More particularly in preferred embodiments the functionalising of the metallic islands uses a solution deposition head such as inkjet print head under automatic control to collect a plurality of functionalising molecules from a corresponding plurality of reservoirs, and to deposit these onto a respective plurality of the metallic islands. In this way an array may be provided with a very large number of different functionalising molecules without the need for special chemistry to attach each one.

As the skilled person will understand, many different types of functionalising molecule may be employed including, but not limited to: oligonucleotides, cDNA, RNA such as mRNA, proteins, antibodies, antigens, and in general anything which binds to a specific biological target molecule (including potential drug molecules).

The same ligand may be used to attach many different functionalising molecules to the metallic nanoparticles. Suitable ligands include, but are not limited to, DSP (dithiobis succinimidyl propionate) and related materials; a streptavidin-biotin link may additionally or alternatively be employed.

In some preferred embodiments the methods of the first and second aspects of the invention provide an array including a plurality of control spots, in particular spots lacking any such functionalising molecules. Preferably these are physically close to the functionalised assay spots, for example less than 200 μm or 100 μm, or 50 μm. Preferably each functionalised spot has an associated control spot. This is important in a very high sensitivity array of the type we describe since the temperature coefficient for refractive index variations can be of order $10^{-3}$ to $10^{-4}/°$ C. and thus even temperature changes of $1/1000°$ C. can have a significant effect on the results. Similarly spatial and temporal variations in the illumination of the array can also have a significant impact on the measured output. In practice without the use of control spots the signal from the array can merely appear to be noise.

In some preferred embodiments the methods of the first and second aspects of the invention provide an array including a plurality of control spots, wherein one or more of said plurality of control spots are configured such that they may detect changes in the bulk refractive index. Changes in the bulk refractive index ($\Delta n$) of the order of $1\times10^{-5}$ or lower refractive index units (RIU) may be detected by appropriately configured control spots.

In accordance with a particularly preferred embodiment the methods of the first and second aspects of the invention provide an array including a plurality of control spots, which are typically regularly spaced spots (for example 30×70 nm) constructed from electron-beam lithography with a pitch typically of the order of 400 nm. A configuration of regularly spaced spots (30×70 nm) constructed from electron-beam lithography in a regular array of pitch 400 nm when illuminated in the near-field configuration of the array reader shows sensitivity to changes in the bulk refractive index of $1\times10^{-5}$ RIU, as demonstrated, for example, by a switch in organic solvent or from water to another solvent such as phosphate buffered saline.

Such one or more control spots provide a specific measure of bulk compositional changes. A control spot sensitive only to bulk refractive index has significant advantages in array design. For example, the refractive index of a blood sample is dominated by the protein load and the bulk refractive index sensor spot will provide a direct measure of blood refractive index and composition. The overall protein load determines the kinetics of non-specific binding so a bulk refractive index determination enables the non-specific binding rate to be predicted. The bulk refractive index can act as a bench-mark for all assay spots. Apparent binding rate constants for each assay on each spot may vary from spot to spot depending on the non-specific binding. Averaging over the total repeats of the assay on the array will produce an empirical rate of binding for the target analyte. The empirical rate may be scaled by the bulk RI to estimate the contribution from non-specific binding. This will inform the confidence in the extracted concentration of the target analyte. Furthermore, during the preparation of the blood sample prior to analysis there may be the addition of other reagents. Variation of the bulk composition may be monitored for composition changes including the addition of the correct sample modifying agents.

In preferred embodiments the substrate provided for use in the methods of the invention includes means for coupling light into the array. Thus in some embodiments the array may be fabricated on a substrate which is configured as a Dove prism. However in some other preferred embodiments light is launched into the edge of a substantially flat, planar substrate which waveguides the light within the thickness of the substrate; such an edge coupling may comprise, for example, a lens on the edge of the substrate or a grating on a surface of the substrate. A waveguided configuration can substantially reduce the cost of the optical components in a practical embodiment of reading apparatus for the array.

In another aspect the invention provides a method of plasmon resonance-based sensing of a plurality of different biological targets simultaneously, the method comprising: coupling light of at least one wavelength into a biosensor array fabricated in accordance with a method of the invention such that total internal reflection of said light at said surface generates an evanescent wave field which excites plasmons in said functionalised metallic nanoparticles and scatters said light; flowing a fluid carrying a plurality of said biological targets for analysis over said array; imaging said scattered light from said array to generate image data for said biological targets carried by said fluid; and analysing said image data to determine levels of said biological targets carried by said fluid.

Thus, in embodiments, we employ a technique which interrogates dark-field scattering from the array rather than analysis of the totally internally reflected light.

In some preferred embodiments the imaging is performed in real time to follow the binding kinetics of the targets. This can generate a time series of data values for each spot, hence facilitating identifying a potential pathological condition by matching binding kinetics additionally or alternatively to a bound level of the target per se. Thus a more accurate "fingerprint" of a condition may be established.

In some preferred embodiments light of two wavelengths is employed, one to either side of a plasmon resonance peak. The signals at these two different wavelengths may then be combined for increased accuracy/sensitivity, in particular by forming a ratio of the signals (intensity changes) at the two different wavelengths. More particularly if the wavelengths straddle the peak then if the peak moves in wavelengths then one signal may go up whilst the other goes down so that forming a ratio (or combining by subtracting) will enhance the combined signal.

The scattering from the array may be viewed from a front side (i.e. the surface carrying the spots) or from a back side (i.e. through the thickness of the substrate towards the spots). Viewing from the back side has the advantage of freeing the top surface for biology without interfering with the optical path. In both cases, however, dark-field scattering is present.

Embodiments of the method may determine a differential binding signal. To see how this works in the case of a functionalised spot, consider the case of an array which has spots of bovine serum albumin, (BSA) and fibrinogen; blood serum may have an antibody to BSA, aBSA but if the animal (or human) from which the blood was obtained needs fibrinogen then no antibody to fibrinogen should be present. Thus binding events will include non-specific binding events for fibrinogen and a combination of non-specific and specific binding events for BSA. Thus it can be seen that in, say, an antibody array some spots may include polyclonal as well as monoclonal antibodies.

Unexpectedly it has been found that compensating signals as described above allow extremely sensitive detection of specific binding events against a high level background of non-specific binding events.

In a further complementary aspect the invention provides a method of plasmon resonance-based sensing of a plurality of different biological targets simultaneously, the method comprising: coupling light of at least one wavelength into a biosensor array fabricated in accordance with a method of the invention such that total internal reflection of said light at said surface generates an evanescent wave field which excites plasmons in said functionalised metallic nanoparticles, said light comprising polarised light with polarisation modulation; detecting an orientation of an elliptical polarisation of said totally internally reflected modulated polarised light; and outputting a target sensing signal dependent on binding of a said biological target to a said functionalising molecule responsive to detection of a change in said elliptical polarisation orientation.

In this specification nanoparticles refers to particles with at least one dimension, preferably two or three dimensions, of less than 1 µm, preferably 500 nm, more preferably 300 nm. Embodiments may have all dimensions less than 1 µm and at least one dimension less than 100 nm.

Features of the above-described embodiments and aspects of the invention may be combined in any permutation.

BRIEF DESCRIPTION OF THE DRAWINGS

These and other aspects of the invention will now be further described, by way of example only, with reference to the accompanying figures in which:

FIG. 1d shows an enlarged image of nanoparticles with a more uniform size distribution than those shown in FIG. 1c.

DETAILED DESCRIPTION OF PREFERRED EMBODIMENTS

Referring firstly to FIG. 1: FIGS. 1a to 1c show a plasmon resonance-based sensing biosensor array at increasing levels of magnification. In FIG. 1c, in particular, it can be seen that rod-like triangular and pancake-shaped (gold) nanoparticles are present. This has advantages as explained further below. Broadly speaking a surface of the type illustrated in FIG. 1c can be fabricated by depositing small seed nanoparticles and then growing larger "crystals" in an environment in which local growth is effectively sterically hindered, for example by a surfactant such as CTAB. FIG. 1d (when viewed in comparison with FIG. 1c) shows the effect of additive metal ions (here $Ag^+$) during the development stage of the first method of the invention, and specifically the closer degree of control possible on the size distribution of resultant particles.

Figure 1A:
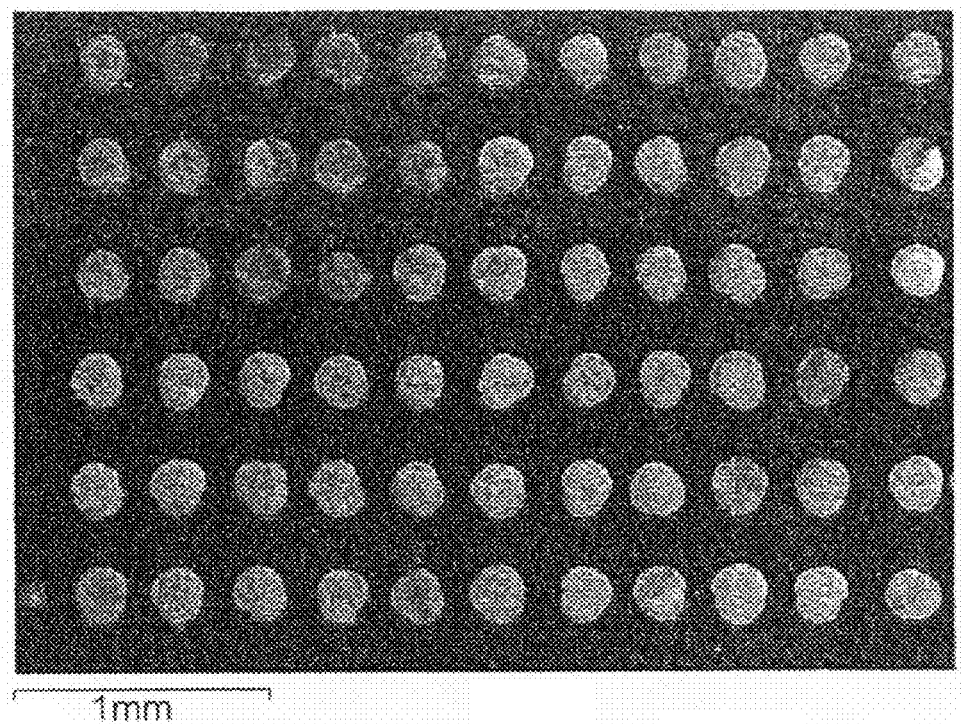
FIGS. 1a to 1d show, respectively, a photograph of an embodiment of a photonic biosensor array fabricated according to an embodiment of the invention, nanoparticles on a metallic island of the array of FIG. 1a, an enlarged image of the nanoparticles of FIG. 1b
Figure 1B:
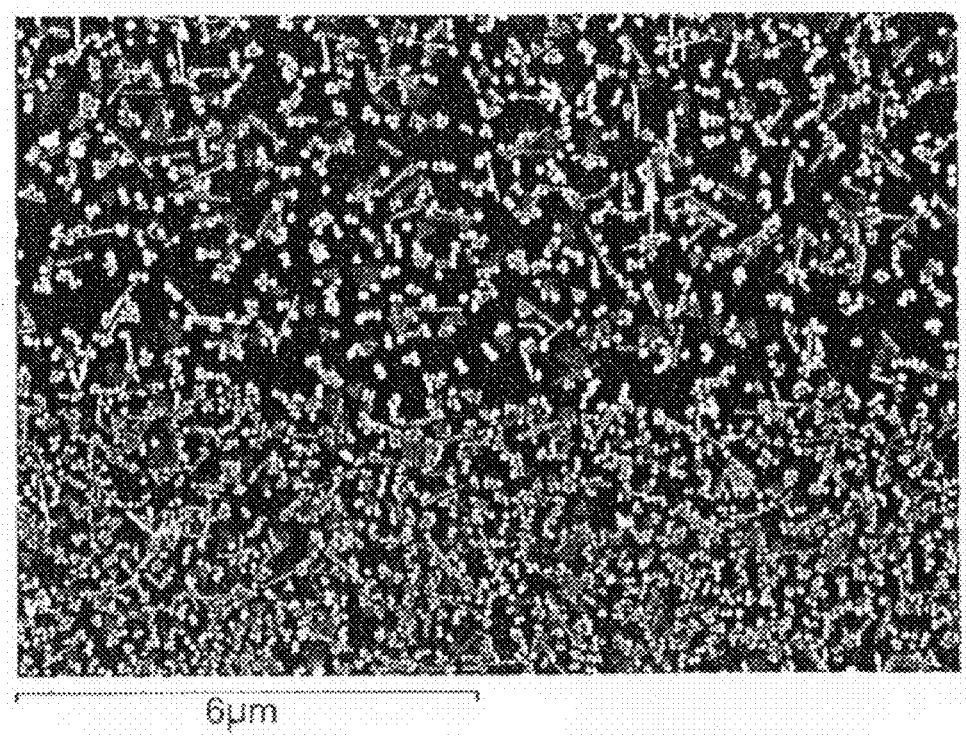
Figure 1C:
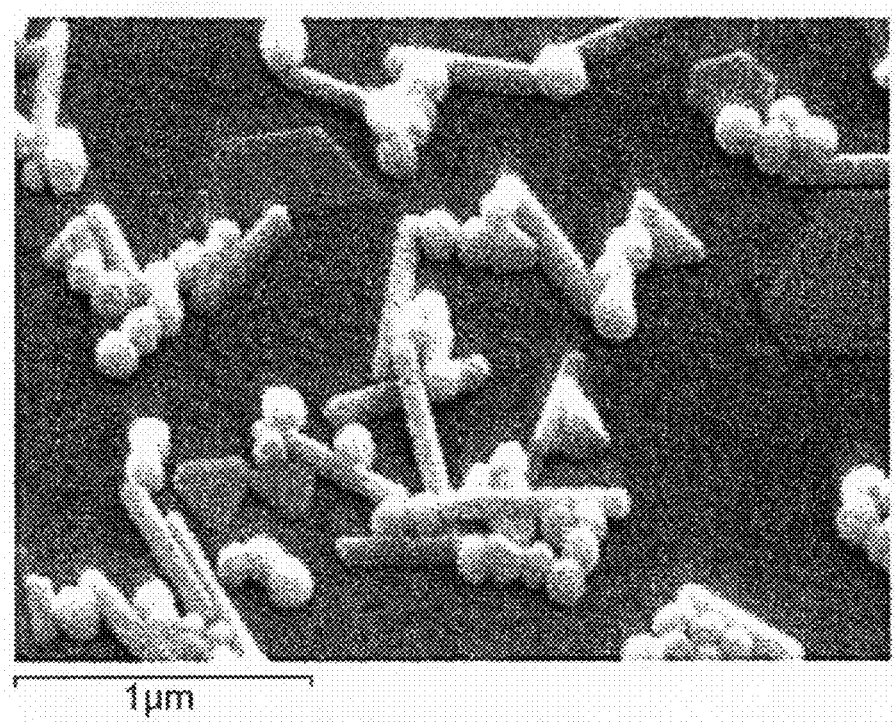
Figure 1D:
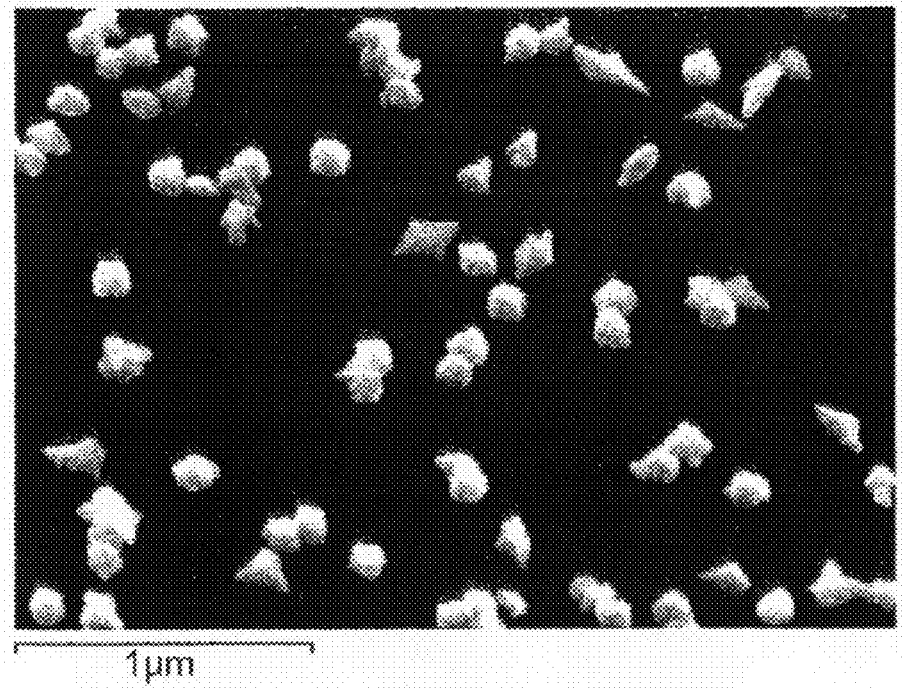
Figure 2A:
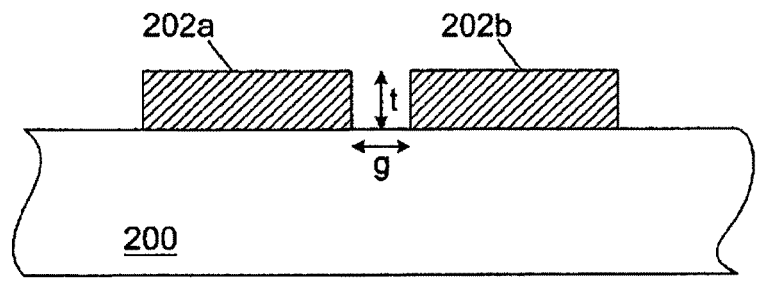
FIG. 2a represents a schematic diagram of a nanoparticle optical antenna, and FIG. 2b a schematic illustration of all alternative configurations of a nanoparticle optical antenna.
Figure 2B:
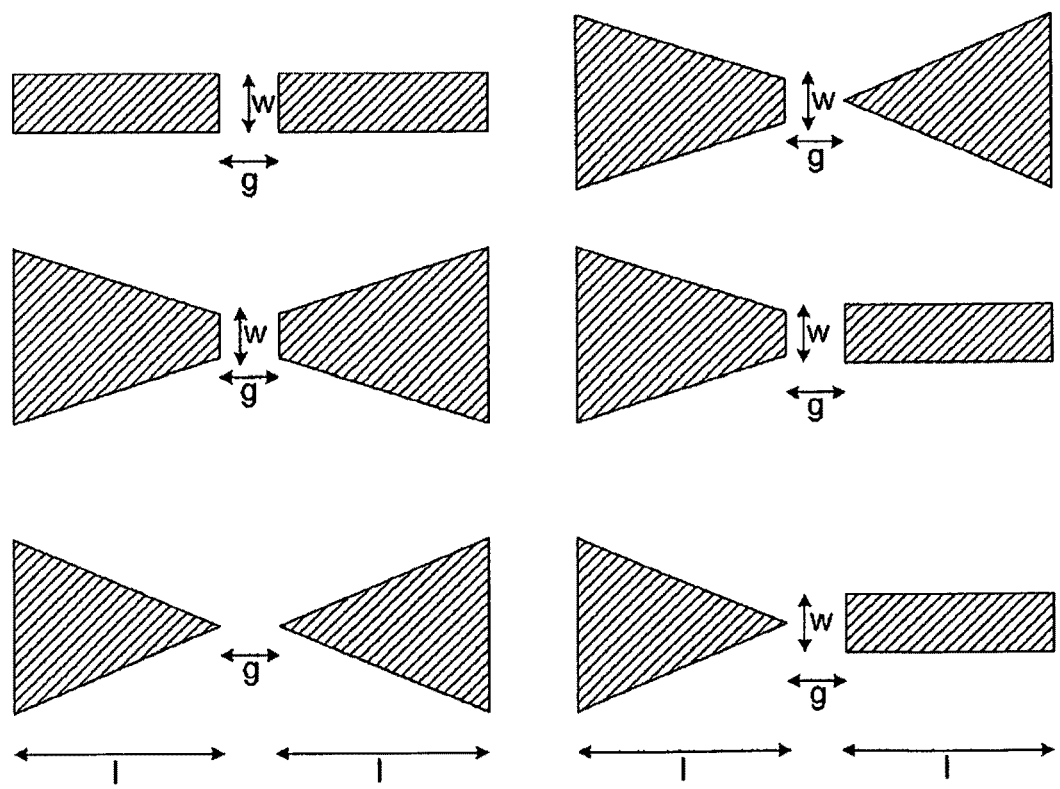

Referring now to FIG. 2a, this shows as pair of rod-like nanoparticles 202a, b on a transparent substrate 200 in vertical cross-section. FIG. 2b shows a view from above showing various alternative configurations for the nanoparticles 202. In some embodiments the length of a nanoparticle, l, may be approximately 130 nm, (a half plasmon wavelength at light wavelength of 830 nm); the dimensions w and t may be in the range 20 nm to 60 nm, for example around 30-50 nm. The gap g between the nanoparticles may be in the region 20 nm to 60 nm, for example around 30 nm. This configuration is believed to substantially enhance the electric field in the gap and hence enhance scattering mediated by plasmon resonance within the nanoparticles, thus increasing the sensitivity of the array.

Figures 3A, 3B, 3C:
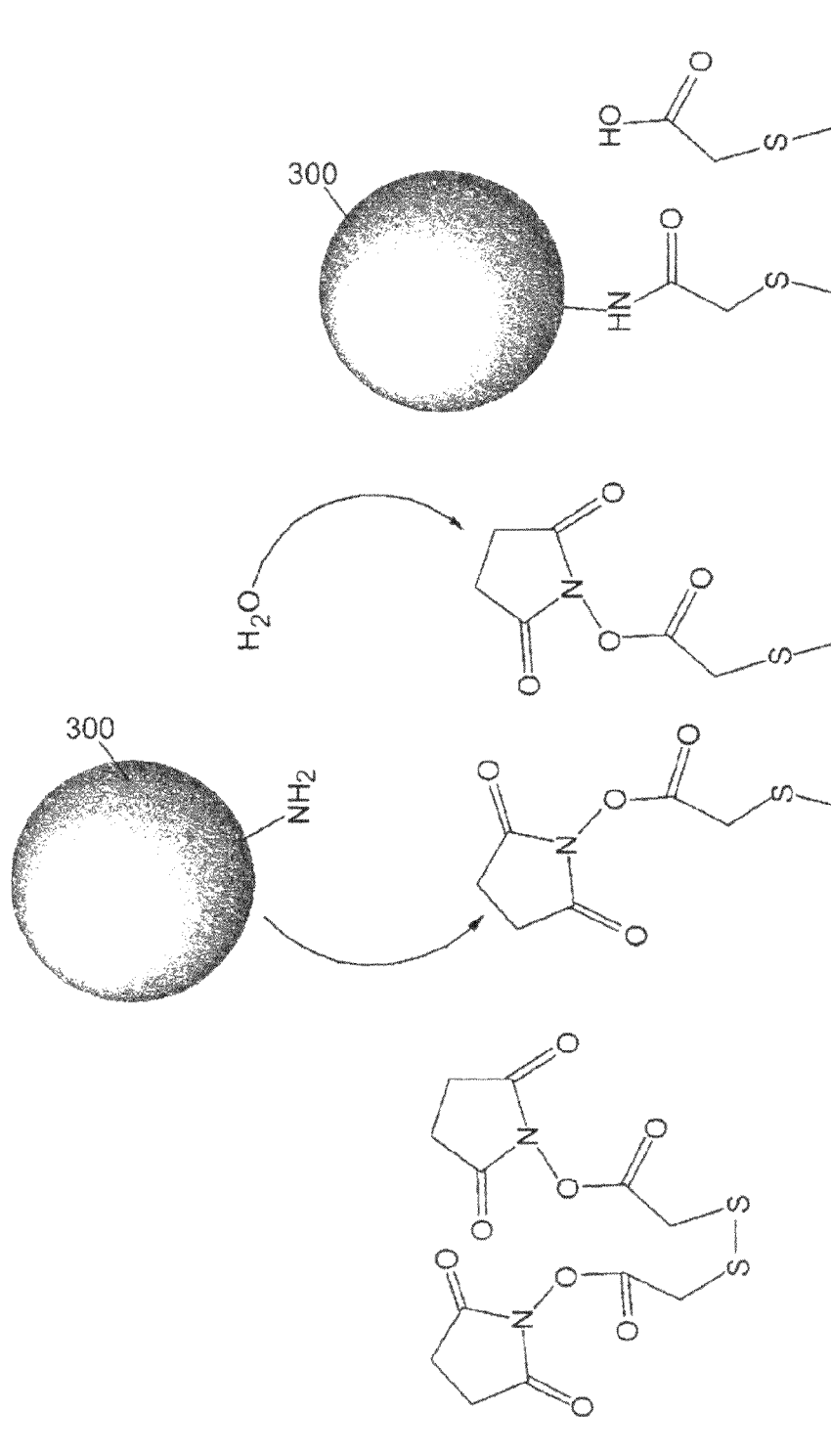
FIGS. 3a to 3c show, respectively, stages in attaching a functionalising molecule to a gold nanoparticle surface.

Having fabricated the nanoparticle islands of the spots for the microarray the nanoparticles are functionalised by attaching biomolecules of any desired type. One preferred procedure using DSP as a linkage is shown in FIGS. 3a to 3c in which a functionalising molecule 300 is shown being attached to a gold nanoparticle surface. The skilled person will understand that other techniques may also be employed for example using a streptavidin-biotin linkage.

Figure 4A:
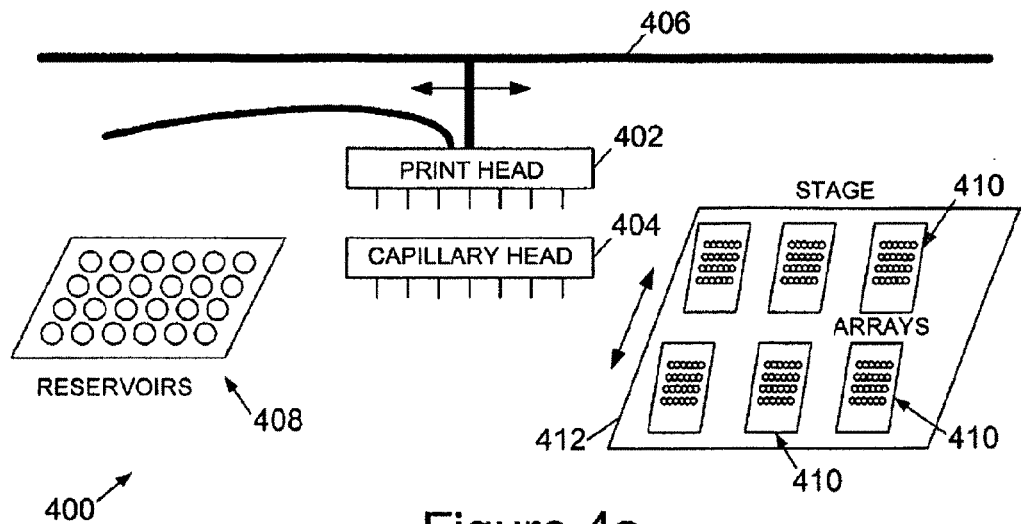
FIGS. 4a to 4c show, respectively, microarray fabrication apparatus for fabricating a microarray in accordance with an embodiment of the invention, and first and second control spot configurations.

FIG. 4a shows apparatus 400 for automatically fabricating a plasmon sensing-based biosensor array according to an embodiment of the invention. In embodiments apparatus 400 comprises an Arrayjet Limited (Edinburgh, UK) Aj 100 instrument which has an inkjet type print head 402 coupleable to a capillary head 404 and movable on a support 406 in one dimension to collect material in solution from a plurality of reservoirs 408 and to deposit the material onto arrays 410 on a movable stage 412. (The control and cleaning mechanism is omitted for clarity).

In operation the apparatus 400 of FIG. 4a is used first to deposit seed gold nanoparticles onto the arrays, which are afterwards developed offline and then replaced on stage 412. Then the reservoirs are replaced with reservoirs containing different functionalising molecules which are then attached to the gold nanoparticles by a straightforward process of selecting the different functionalising molecules from reservoirs 408 and depositing these onto the assay spots on the arrays 410. By contrast with fluorescence-labelling techniques common linkage chemistry can be used for a wide range of different functionalising molecules, thus enabling automation of the functionalisation process. The inkjet print head 402 facilitates non-contact printing, thus preventing damage to the assay spots.

Figure 4B:
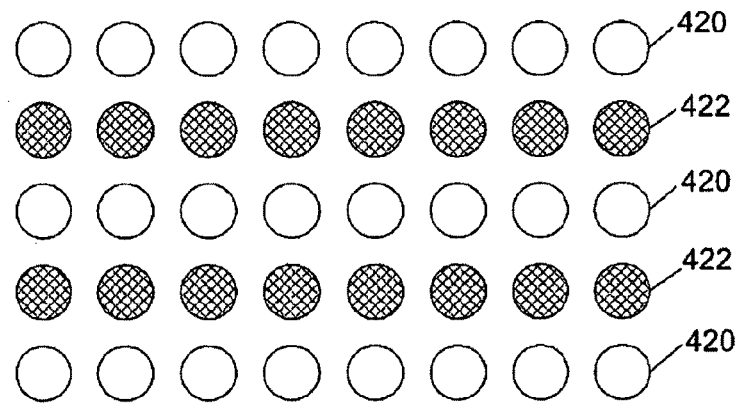
Figure 4C:
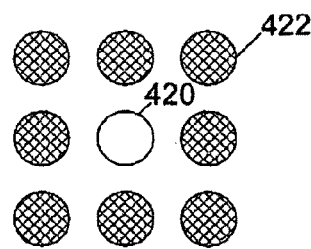

FIG. 4b shows spots on an array 410 illustrating one example configuration of assay spots 420 and associated control spots 422. FIG. 4c illustrates an alternative configuration. In practice it has been found important that the control spots are physically close to the assay spots, to enable good compensation for variations in parameters such as temperature, flow over the microarray, and illuminating light beam uniformity. Preferably at least one control spot is within 100 µm, preferably within 50 µm of an assay spot.

Figure 5:
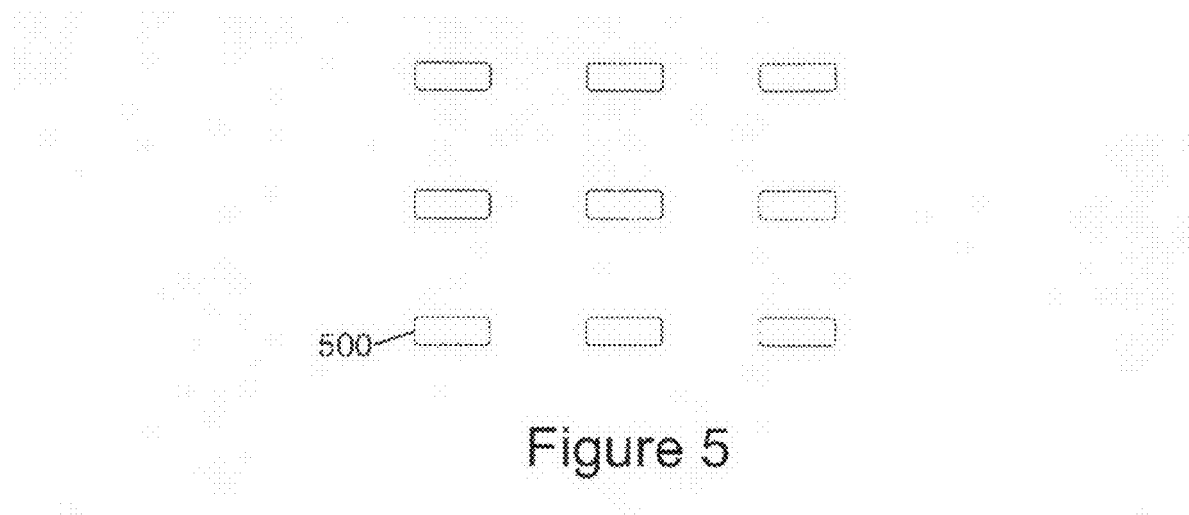
FIG. 5 shows a control spot configuration for 30×70 nm gold rods with a pitch of 400 nm in accordance with an embodiment of the invention.

FIG. 5 shows a control spot configuration for 30×70 nm gold rods, 500, with a pitch of 400 nm in accordance with an embodiment of the invention. It has been found that such a configuration of regularly spaced spots (30×70 nm) constructed from electron-beam lithography in a regular array of pitch 400 nm when illuminated in the near-field configuration of the array reader shows sensitivity to changes in the bulk refractive index of $1\times10^{-5}$ RIU. This is demonstrated by a switch in organic solvent and from water to phosphate buffered saline. When viewed normal to the surface there is no change in the scattered radiation intensity and therefore does not show sensitivity to binding proteins onto the gold surface and in this regard it is an excellent control spot for bulk compositional changes.

Figure 6:
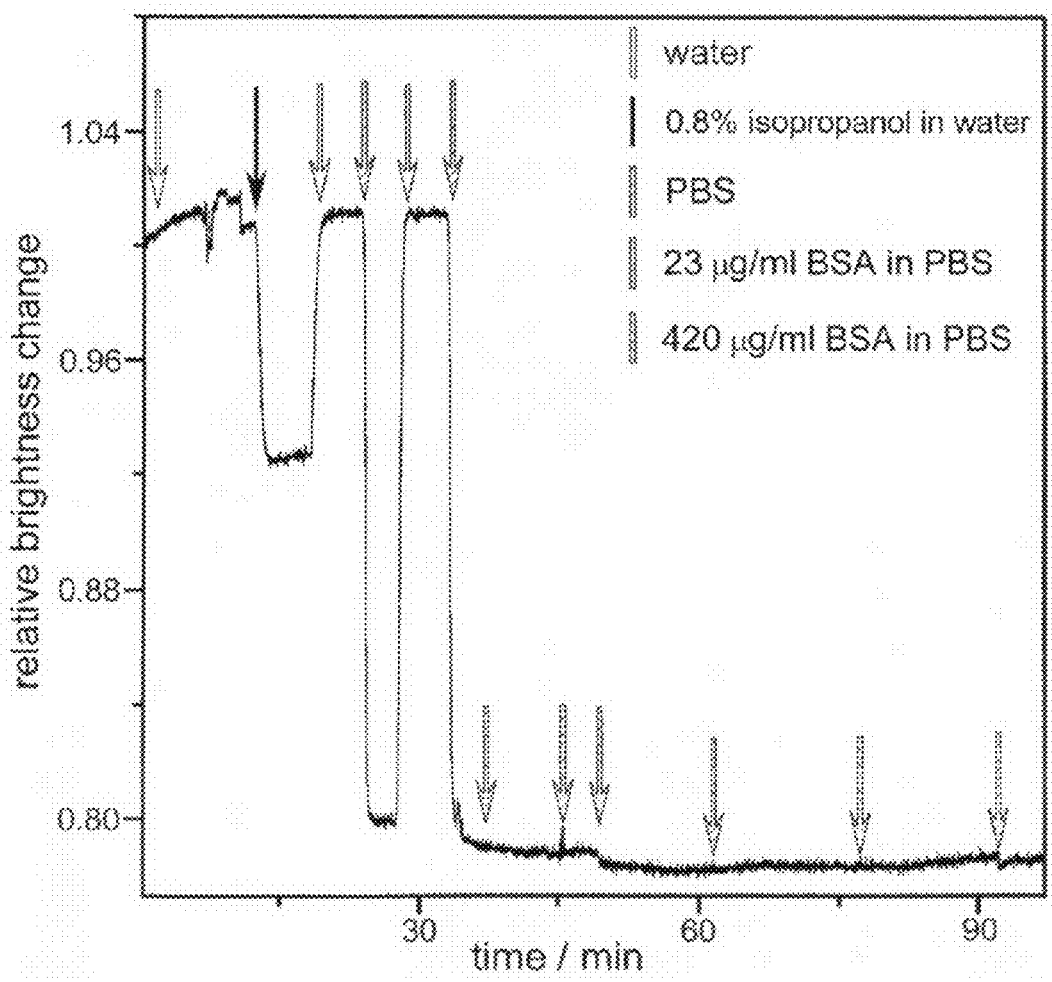
FIG. 6 illustrates the sensitivity to changes in the bulk refractive index achievable by use of appropriate control spot configuration, as evidenced by a switch in the solvent, in accordance with an embodiment of the invention.

FIG. 6 illustrates the sensitivity to changes in the bulk refractive index achievable by the use of the control spot configuration shown in FIG. 5. The range of solvents used to evidence the effect are indicated. The effect is presented in terms of relative brightness change. Such one or more control spots provide a specific measure of bulk compositional changes. A control spot sensitive only to bulk refractive index has significant advantages in array design. For example, the refractive index of a blood sample is dominated by the protein load and the bulk refractive index sensor spot will provide a direct measure of blood refractive index and composition. The overall protein load determines the kinetics of non-specific binding so a bulk refractive index determination enables the non-specific binding rate to be predicted. The bulk refractive index can act as a bench-mark for all assay spots. Apparent binding rate constants for each assay on each spot may vary from spot to spot depending on the non-specific binding. Averaging over the total repeats of the assay on the array will produce an empirical rate of binding for the target analyte. The empirical rate may be scaled by the bulk RI to correct estimate the contribution from non-specific binding. This will inform the confidence in the extracted concentration of the target analyte. Furthermore, during the preparation of the blood sample prior to analysis there may be the addition of other reagents. Variation of the bulk composition may be monitored for composition changes including the addition of the correct sample modifying agents.

A substance to be analysed, for example blood serum, may be provided to the microarray for sensing by, for example, a syringe coupled to a duct above the array spots to flow the substance, for example serum, over the microarray. Embodiments of the apparatus permit samples of bloody fluid to be analysed directly (optionally diluted, for example with saline) because, in embodiments the use of some spots as controls enables compensation for non-specific binding. In more sophisticated embodiments a microfluidic fan-out along one or more edges of the array of spots may be provided.

Thus we have described a method for the fabrication of a plasmon resonance-based biosensing microarray which in embodiments employs discrete islands of conductive nanoparticles and which, in embodiments, is viewed in a dark-field scattering arrangement, preferably at two wavelengths one to either side of the resonant peak, preferably with at least some of the spots being used as controls. This combination of features enables a combination of both very high sensitivity and also selectivity, more particularly discrimination against non-specific binding events. By following binding kinetics of a plurality of targets over time using such a microarray a characteristic fingerprint of a condition may be obtained based upon a multi-dimensional data set comprising time series data indicative of binding kinetics for a plurality of characterising targets. This multidimensional data may be fitted to one or more corresponding templates to identify the condition with a high degree of accuracy and sensitivity.

Thus aspects related to the invention provide methods and apparatus to perform such an identification of a condition by fitting multi-dimensional data, in particular from a plasmon resonance-based biosensing microarray as described above.

No doubt many other effective alternatives will occur to the skilled person. It will be understood that the invention is not limited to the described embodiments and encompasses modifications apparent to those skilled in the art lying within the spirit and scope of the claims appended hereto.

EXAMPLES

An example procedure for seed-mediated growth of gold nanoparticles on silica or glass surface is as follows:

1. 3-4 nm spherical seeds are produced by reduction of $Au^{3+}$ ($3\times10^{-4}$ M $HAuCl_4$) by excess of $NaBH_4$ ($3\times10^{-3}$ M) in the presence of tri-sodium citrate capping agent ($3\times10^{-4}$ M).
2. Seed particle colloid is printed in array of spots on the uncoated silica or glass surface and the slides are allowed to dry. The printed seed density (in terms of number of particles per unit of surface area) determines the density of the grown particles, therefore one can easily achieve practically any desired surface coverage (which can, of course be varied from spot to spot to produce kind of monochrome image).
3. The seeded slides are washed in water to remove excess of citrate and any particles which were not adhered to the surface.
4. The seeded slides are developed in grown solution containing $2\times10^{-4}$ M $HAuCl_4$, 0.1M cetyltrimethylammonium bromide (CTAB) as capping agent, and $4\times10^{-4}$ M ascorbic acid as reducing agent for 20-30 minutes at 25° C. producing the variety of gold nano-shapes (shown in FIG. 1c). In the presence of $1\times10^{-5}$ M $Ag^+$ the size distribution of grown particles is more uniform and gold nanocrystals are highly faceted, which can improve sensitivity to the change of the medium refractive index (shown in FIG. 1d).

The invention claimed is:

1. A method for the fabrication of a biosensor array for plasmon resonance-based sensing of a plurality of different biological targets simultaneously, the method comprising:
   (i) providing a transparent substrate;
   (ii) providing seed metallic nanoparticles in the form of a colloid;
   (iii) depositing said colloid as discrete metallic islands on the transparent substrate, each of said metallic islands comprising a plurality of metallic nanoparticles;
   (iv) washing the substrate in order to remove unadhered material;
   (v) developing the substrate in a growth solution, which solution comprises a salt of the same metal which is present in the form of discrete metallic islands on the substrate, a reducing agent, a capping agent and optionally a surfactant;
   (vi) washing the developed substrate; and
   (vii) functionalising each of said metallic islands with a different functionalising molecule using a common chemical process to attach said different functionalising molecules to said metallic islands,
   wherein said metallic islands of said array are spaced apart, arranged at intervals of at least 0.1 mm, and
   wherein within a said metallic island said plurality of metallic nanoparticles comprise a discontinuous layer of individual, multi-faceted nanoparticles.

2. A method as claimed in claim 1, wherein the substrate comprises an uncoated silica/glass surface.

3. A method as claimed in claim 1, wherein the metallic nanoparticles comprise copper, silver, gold, platinum, palladium or iridium or a mixture or an alloy thereof.

4. A method as claimed in claim 1, wherein, in step (ii), the seed metallic nanoparticles provided in the form of a colloid are substantially spherical with a diameter in the range of from 2 to 6 nm.

5. A method as claimed in claim 1, wherein, in development step (v), the growth solution comprises a metal salt, a reducing agent, a capping agent and a surfactant.

6. A method as claimed in claim 1, wherein, in development step (v), the growth solution comprises a metal salt, a reducing agent, and the capping agent cetyltrimethylammonium bromide (CTAB).

7. A method as claimed in claim 1 wherein said metallic nanoparticles comprise gold nanoparticles.

8. A method as claimed in claim 7, wherein, in the development step (v), the gold salt comprises $HAuCl_4$ or a potassium, calcium, sodium, or lithium salt thereof.

9. A method as claimed in claim 7, wherein, in the development step (v), the capping agent is CTAB and the reducing agent is ascorbic acid.

10. A method as claimed in claim 1, wherein functionalising step (vii) comprises using a solution deposition head with a plurality of nozzles to collect a plurality of said different functionalising molecules from a plurality of reservoirs and to deposit said plurality of functionalising molecules onto a respective plurality of said metallic islands.

11. A method as claimed in claim 10, wherein said different functionalising molecules are attached to said metallic nanoparticles using the same ligand.

12. A method as claimed in claim 10, wherein, in functionalising step (vii), a fraction of the respective plurality of said metallic islands are left un-functionalised and instead comprise a plurality of control spots.

13. A biosensor array for plasmon resonance-based sensing of a plurality of different biological targets, the array made by the fabrication method of claim 1, the biosensor array comprising a transparent substrate having a surface bearing a plurality of array spots for plasmon resonance sensing, each of said array spots comprising a discrete metallic island to which is attached functionalising molecules for binding to a biological target, different said islands bearing different said functionalising molecules for binding to different ones of said biological targets, and wherein total internal reflection of light at said surface at a wavelength at or near a said plasmon resonance results in scattering of said light away from said surface, said scattering being modulated by said binding of said biological targets.

14. A biosensor array as claimed in claim 13 wherein said metallic nanoparticles have at least one dimension of less than 30 nm.

15. A biosensor array as claimed in claim 13 wherein said nanoparticles comprise rod-like nanoparticles.

16. A biosensor array as claimed in claim 13 wherein said nanoparticles include nanoparticles forming an optical antenna for said light wherein said optical antenna comprises an adjacent pair of nanoparticles having a generally rod-like or triangular shape, and having adjacent ends separated by a gap of less than 100 nm, preferably less than 50 nm, said nanoparticles having physical lengths which are resonant for a said plasmon resonance at substantially the same optical wavelength.

17. A biosensor array as claimed in claim 13 further comprising a plurality of control spots, a said control spot substantially lacking said functionalising molecules.

18. A biosensor array as claimed in claim 17 wherein a said control spot is capable of detecting a change in the bulk refractive index ($\Delta n$) of the order of $1\times10^{-5}$ or lower refractive index units (RIU).

19. A biosensor array as claimed in claim 13 wherein said different functionalising molecules are attached to said metallic nanoparticles using the same ligand.

20. A biosensor array as claimed in claim 13 wherein said metallic nanoparticles comprise gold nanoparticles.

* * * * *